United States Patent
Dávila García et al.

(10) Patent No.: US 12,239,315 B2
(45) Date of Patent: Mar. 4, 2025

(54) TRANSVAGINAL LIFT DEVICE FOR PROLAPSED PELVIC ORGAN

(71) Applicants: Hugo H. Dávila García, Vero Beach, FL (US); Raúl E. Storey Rojas, Vero Beach, FL (US); Mariano Enrique Cordero Segura, San Jose (CR); Víctor Manuel Solano Umaña, San Jose (CR); Isaías Herrera Jiménez, San Jose (CR)

(72) Inventors: Hugo H. Dávila García, Vero Beach, FL (US); Raúl E. Storey Rojas, Vero Beach, FL (US); Mariano Enrique Cordero Segura, San Jose (CR); Víctor Manuel Solano Umaña, San Jose (CR); Isaías Herrera Jiménez, San Jose (CR)

(73) Assignee: Arcus Medical LLC, Vero Beach, FL (US)

( * ) Notice: Subject to any disclaimer, the term of this patent is extended or adjusted under 35 U.S.C. 154(b) by 158 days.

(21) Appl. No.: 18/112,667

(22) Filed: Feb. 22, 2023

(65) Prior Publication Data
US 2024/0277332 A1    Aug. 22, 2024

(51) Int. Cl.
*A61B 17/04*    (2006.01)
*A61B 1/32*    (2006.01)

(52) U.S. Cl.
CPC ............ *A61B 17/0469* (2013.01); *A61B 1/32* (2013.01); *A61B 17/0401* (2013.01);
(Continued)

(58) Field of Classification Search
CPC ... A61B 1/303; A61B 1/307; A61B 2217/005; A61B 17/0401
See application file for complete search history.

(56) References Cited

U.S. PATENT DOCUMENTS

| | | | | |
|---|---|---|---|---|
| 786,457 | A | * | 4/1905 | McGinnis ................ A61B 1/32 600/211 |
| 2,504,202 | A | * | 4/1950 | Kadavy ................ A61B 17/062 606/147 |

(Continued)

FOREIGN PATENT DOCUMENTS

CN    112869709 A    6/2021

OTHER PUBLICATIONS https://emedicine.medscape.com/article/1848619-overview; website known prior to Feb. 22, 2023.
(Continued)

*Primary Examiner* — Dianne Dornbusch
(74) *Attorney, Agent, or Firm* — Reinhart Boerner Van Deuren P.C.

(57) ABSTRACT

A transvaginal lift device that includes a speculum having an upper vane and a lower vane. The upper and lower vanes are each elongate with a front end and a rear end. Further, the upper and lower vanes are attached at the rear end such that the two vanes move between a closed position and an open position. Specifically, the upper vane has an opening/window configured to allow prolapsed tissue to protrude through the opening/window into an interior portion of the speculum. A suturing instrument includes a needle cannula and a suture. The suturing instrument is attached to the speculum. Furthermore, the suturing instrument is configured to place the suture in the prolapsed tissue protruding through the opening/window.

25 Claims, 14 Drawing Sheets

(52) U.S. Cl.
CPC ............. *A61B 2017/0409* (2013.01); *A61B 2017/0464* (2013.01); *A61B 2017/047* (2013.01); *A61B 2017/0496* (2013.01); *A61B 2217/005* (2013.01)

(56) References Cited

U.S. PATENT DOCUMENTS

| | | | |
|---|---|---|---|
| 8,128,640 B2 * | 3/2012 | Harris | A61B 17/0469 606/139 |
| 8,506,503 B2 | 8/2013 | Fritscher-Ravens et al. | |
| 8,562,631 B2 | 10/2013 | Saliman et al. | |
| 8,979,873 B2 | 3/2015 | Singhatat et al. | |
| 9,089,320 B2 | 7/2015 | Spivey et al. | |
| 9,795,375 B2 | 10/2017 | Lore et al. | |
| 10,182,843 B2 | 1/2019 | Williams | |
| 10,201,343 B2 | 2/2019 | Tong et al. | |
| 10,299,828 B2 | 5/2019 | Goldberg et al. | |
| 10,492,792 B2 | 12/2019 | Catanese, III et al. | |
| 10,667,802 B2 | 6/2020 | Zoll et al. | |
| 10,932,769 B2 | 3/2021 | Viola | |
| 2009/0125010 A1 * | 5/2009 | Sharkey | A61B 18/04 606/27 |
| 2011/0202074 A1 | 8/2011 | Talmo et al. | |
| 2012/0265058 A1 | 10/2012 | Carrascosa | |
| 2013/0023723 A1 | 1/2013 | Mittal et al. | |
| 2017/0348085 A1 | 12/2017 | Harari | |
| 2019/0059948 A1 | 2/2019 | Kim et al. | |

OTHER PUBLICATIONS

Davila HH, Deshommes H, Paul A, Abdelhameed S, Filippi C, Bello L, MalaveHuertas D, Bigay F, Bruce L, Goodman L, Gallo T, Fyffe G. Evaluation of the Pubocervical Fascia With 3-Dimensional Endovaginal Ultrasonography and Correlation With Intraoperative Findings During Robotic Sacrocervicopexy. Urology. Dec. 2021;158:81-87. doi: 10.1016/j.urology.2021.05.033. Epub Jun. 4, 2021. PMID: 34090888.

Davila, H.H., Abdelhameed, S., Malave-Huertas, D. et al. Ultrasonography and robotic-assisted laparoscopic sacrocervicopexy with pubocervical fascia reconstruction: comparison with standard technique. J Robotic Surg 14, 759-766 (2020).

Davila, H.H., Brown, K., Dara, P. et al. Robotic-assisted laparoscopic apical suspension: description of the spiral technique. J Robotic Surg 13, 519-523 (2019).

Davila HH, Bruce L, Goodman L, Gallo T Robotic Assisted Laparoscopic Apical Suspension. Description of a 4 Points Technique (RALAS-4): First Case Reported. Open Journal of Obstetrics and Gynecology. vol. 7 No. 9, Sep. 2017.

* cited by examiner

TRANSVAGINAL LIFT DEVICE FOR PROLAPSED PELVIC ORGAN

FIELD OF THE INVENTION

This invention generally relates to medical devices and, in particular, to medical devices used for examination, positioning, suturing, repairing and tensioning tissue.

BACKGROUND OF THE INVENTION

In a Women's Health Initiative study, investigators found a 41% prevalence of pelvic organ prolapses during standard physical examination in postmenopausal women older than 60 years who had not had a hysterectomy. Approximately 300,000 surgeries are performed every year to correct pelvic organ prolapses in the United States alone. The cost of these surgeries is more than $1 billion.

Non-surgical method for treating this condition include the use of vaginal pessaries for both diagnostic and therapeutic purposes. Pessaries are often used to relieve symptoms of prolapse and of urinary stress incontinence. They are less costly than surgery for in the treatment of pelvic organ prolapse. However, in up to 30% of cases, the pessaries are not fitted correctly to the patient. Furthermore, in 25% to 40% of patients treated with this method experience, the symptoms of pelvic organ prolapse are not relieved. Therefore, it would be desirable to have a method and device for the treatment of pelvic organ prolapse that is more effective and less costly than those described above.

Embodiments of the invention provide such a method and device for the treatment of pelvic organ prolapse. These and other advantages of the invention, as well as additional inventive features, will be apparent from the description of the invention provided herein.

BRIEF SUMMARY OF THE INVENTION

Embodiments of the present invention relate to a medical device, in particular to a vaginal speculum device designed to lift and prepare the prolapsed tissue to be sutured with a device designed to repair the vaginal prolapse. The suturing device and the vaginal speculum are used together for opening the vagina, generating a vacuum to expose a specific section of the vaginal prolapse through an opening in the speculum, and to perform the suture and tensioning of the prolapse with different types of sutures with anchors or implants with anchors. The intent of the vaginal speculum is to open the vagina and prepare the tissue to be repaired with the suturing device, by deploying a suture or implant inside the prolapsed tissue along the vaginal wall. Anchors are attached to, or a part of, the suture or implant. Once the suture with anchors or implants with anchors are implanted inside the prolapsed tissue, the suture or implant is pulled to tension the tissue and to lift the wrinkles of the prolapsed tissue, in order to restore the correct, natural vaginal form. The suture, implants and anchors could be permanent implants, or may be made of bio-resorbable materials that will be absorbed after the prolapsed tissue has been corrected, also, the suture or implant may be made of materials with or without elastomeric properties.

In one aspect, the invention provides a medical device that includes two main instruments or devices. The first device is a suturing instrument; and the second device is a speculum specifically designed to lift the tissue and to prepare it to be repaired and support the suturing instrument in specific and desired positions during the suturing procedure. The structure of both elements is designed to provide a safe, effective, and standardized suture. More specifically, the speculum has features designed to position the prolapsed tissue in a particular location, prepare the prolapsed tissue for repair, and to control and standardize the needle cannula and suture placement. As will be shown below, the speculum is designed such that it can be fixed in specific positions in order to lift the tissue, position the tissue in the opening or window of the speculum vane, prepare the tissue for repair, and to allow for an accurate and repeatable suture.

In particular, the first and second devices are designed to be used together to repair a pelvic organ prolapse. The suturing instrument may have different configurations with respect to the type of suture used in the suturing instrument, and with respect to the suturing technique to be used. Some configurations deploy the suture during the insertion of the needle, while other configurations insert the needle and deploy the suture when the needle is taken out. The intent is not to limit the different suturing configurations and techniques that may be developed and performed using this device.

As will be explained below, embodiments of the transvaginal lift device may include a low-cost, disposable, or reusable speculum that works together with the suturing instrument to open the vaginal area and perform the suture through an innovative window and a vacuum system located on the upper piece of the speculum to solve the problem to access and standardize the position of the prolapse tissue. The size of the window is not limited since this can be modified to repair different levels of prolapsed tissue. In a particular embodiment, the speculum comprises two interconnected vanes or blades. In certain embodiments, that speculum has an adjusting screw, so that the blades or vanes can be opened and fixed in a particular open position (i.e., such that the extent of the opening does not change) in order to dilate the vagina for accessing the condition of the vaginal prolapse through the innovative opening/window located on the upper vane of the speculum, also, in some embodiments, the speculum has a vacuum system to ensure the tissue is pulled into the window and is prepared for the repair.

In another aspect, the invention provides a transvaginal lift device that includes a speculum having an upper vane and a lower vane. The upper and lower vanes are attached at the rear end that allows the movement, such that the vanes move between a closed position and an open position. Additionally, in certain embodiments, the upper vane has a window configured to allow prolapsed tissue to protrude through the window into an interior portion of the speculum. A suturing instrument includes an inner needle cannula. As explained below, some embodiments include an external pusher cannula to tighten the tissue, and a suture. The suturing instrument may be attached to the speculum. Furthermore, the suturing instrument is configured to place the suture in the prolapsed tissue protruding through the opening/window.

In certain embodiments, the lift device has a vacuum system to pull the prolapse tissue into the window and locate it in a specific position to be repaired, the vacuum may be generated using a syringe or compressed air. In particular embodiments, the vacuum system is located in the upper vane, which has the opening/window, while in alternate embodiments, the vacuum system is located between the upper and lower vanes, or in the opening/window. When in the upper vane, the vacuum system may include a speculum cover attached to the upper vane. The speculum cover is configured to provide a vacuum seal where it is attached to the upper vane. Also, the vacuum system may be adjustable or removable with respect to the speculum.

In a particular embodiment, the suturing instrument includes an external pusher cannula inside of which the needle cannula is disposed, the external pusher cannula configured to support the tissue during the tensioning step, while the suture or implant is tensioned. In certain embodiments, the external pusher cannula has a handle for manual manipulation of the external pusher cannula. Furthermore, in some embodiments, the suturing instrument includes an inner pusher rod disposed within the needle cannula, the inner pusher rod configured to deploy the anchors and suture or implant during the procedure.

In particular embodiments, the inner pusher rod has a handle for manual manipulation of the inner pusher rod. In other embodiments, the needle cannula and the inner pusher rod are configured to deploy the suture or implant having one or more attached anchors for tensioning of the prolapsed tissue. The one or more anchors may be cylindrical or spherical to facilitate insertion into and deployment from the needle cannula. In other embodiments, the one or more anchors may each be made from one or more wires. Alternate embodiments of the transvaginal lift device include the needle cannula and the inner pusher rod configured to deploy the suture having one or more knots in the suture along a length thereof. The one or more knots are for tensioning of the prolapsed tissue Furthermore, the needle cannula may also have a handle for manual manipulation of the needle cannula. In more particular embodiments of the invention, the speculum includes a handle to control the opening and closing the upper and lower vanes. Moreover, the speculum handle may include an adjusting screw configured to fix the extent of the open position of the upper and lower vanes.

The window may vary in shape and size. In certain embodiments, the window is rectangular, while in alternate embodiments, the window is circular or elliptical, and in more particular embodiments the window is adjustable to improve the positioning and access to the prolapsed tissue. In some embodiments of the lift device, the speculum includes a lighting element, which may be an LED lighting element. In more particular embodiments, the lighting element is battery-powered.

The vacuum system, as part of the speculum, may vary in shape, size, and pressure. In certain embodiments, the vacuum system may be located in the upper vane to ensure the tissue is suctioned into the window and the elements that generates the vacuum may be adjusted and removed as needed, while in alternate embodiments, the vacuum system is located between the vanes or in the window, and in more particular embodiments, the vacuum system is adjustable, removable or used while the suturing process is performed to ensure the tissue is positioned in the right position and the accurate penetration of the tissue is warranted.

In a further embodiment, the speculum includes a guide to fix a position of the needle cannula. The guide may be attached to the upper vane of the speculum. In particular embodiments, the guide has an opening through which the needle cannula is placed or inserted. In more particular embodiments, an external pusher cannula may be inserted through the guide opening and an inner pusher rod inside the needle cannula.

The suture or implant may include one or more anchors for tensioning the prolapsed tissue. Furthermore, the one or more anchors may be formed in a variety of shapes, where the particular shape depends on the suturing application and technique being used. Additionally, the suture or implant may be made of resorbable or non-resorbable material, also, may be made of elastomeric or non-elastomeric material.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Embodiments of the invention disclosed herein include a transvaginal lift device which can be used to treat two medical conditions: pelvic organ prolapse; and stress urinary incontinence. As will be explained in detail below, the transvaginal lift device works in conjunction with a modified and unique speculum, which provide may provide both illumination and support to perform an accurate suture. In some embodiments, the modified speculum has a specific guide to standardize the needle placement. As will also explained below, this modified speculum provides visibility and freedom to perform the suture with the speculum in a specific point and in a standardize manner. Thus, it will be shown that the transvaginal lift device is a cost-effective device that reduces the risk and procedure time with respect to the treatment of pelvic organ prolapse or stress urinary incontinence.

Figure 1:
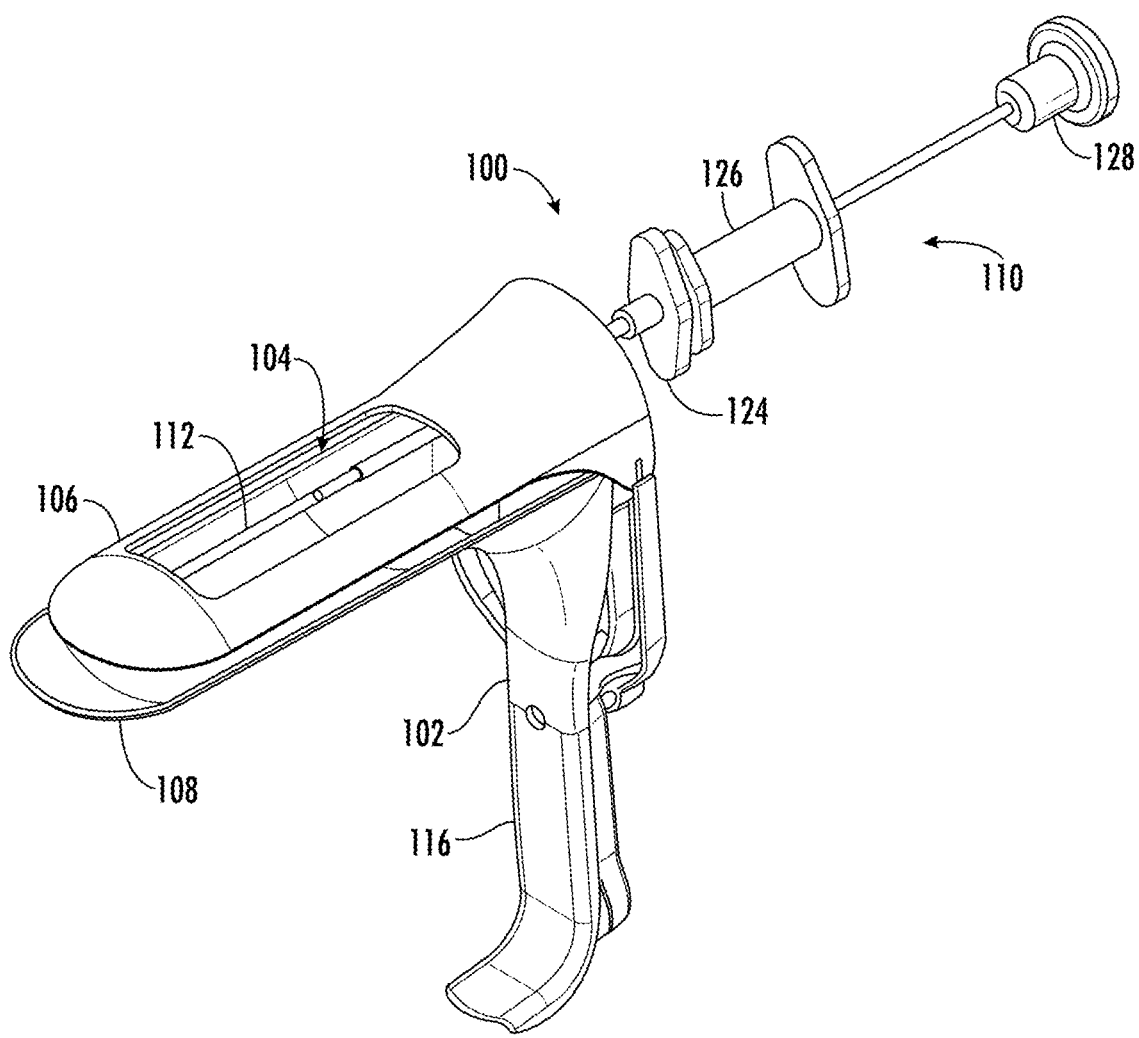
FIG. 1 is a perspective view of a transvaginal lift device having a speculum with an upper window and an assembled suturing instrument, in accordance with an embodiment of the invention.
Figure 2:
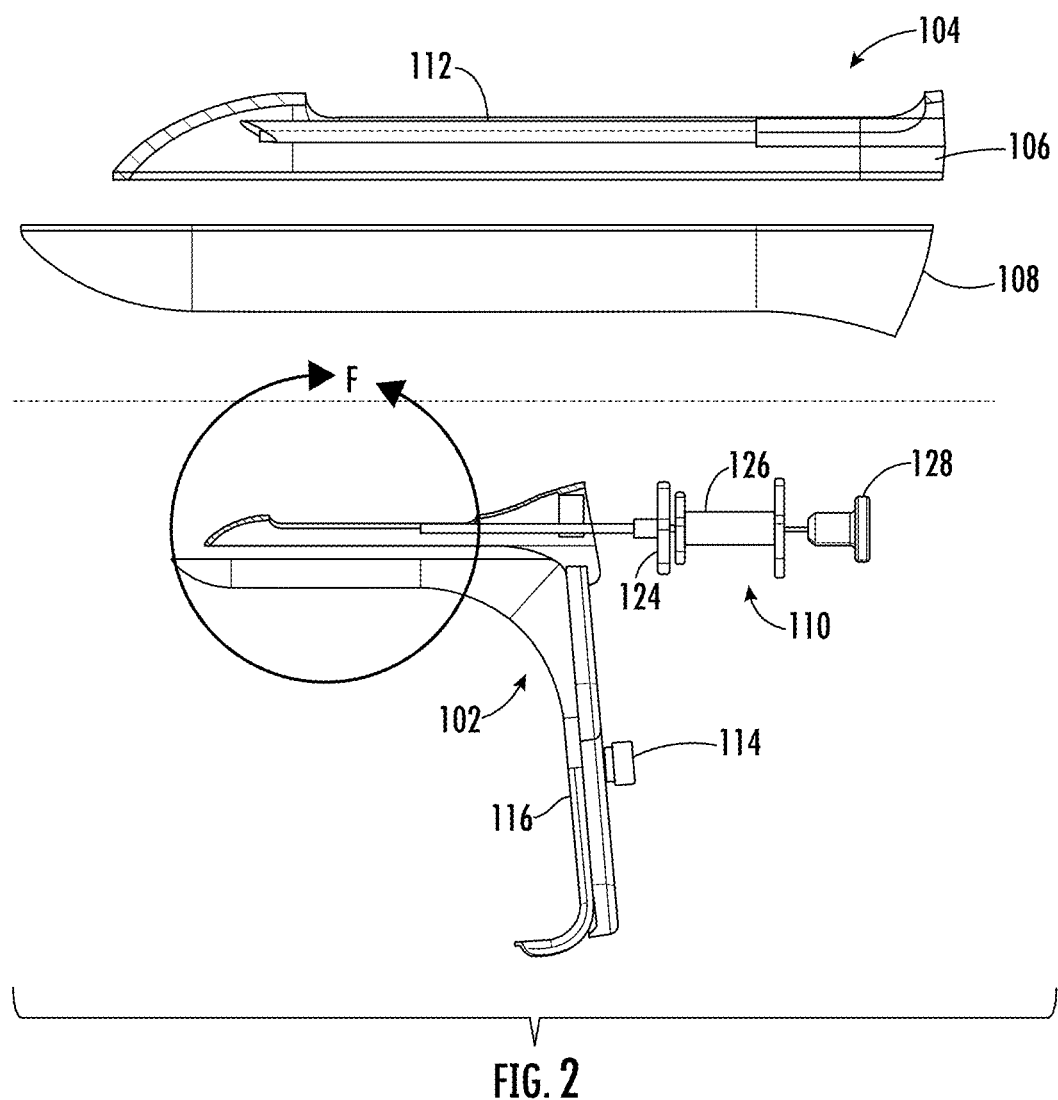
FIG. 2 is a side view of the transvaginal lift device as it is used with the suturing instrument and the needle cannula passing through the speculum and including an enlarged view of the speculum, according to an embodiment of the invention.
Figure 3:
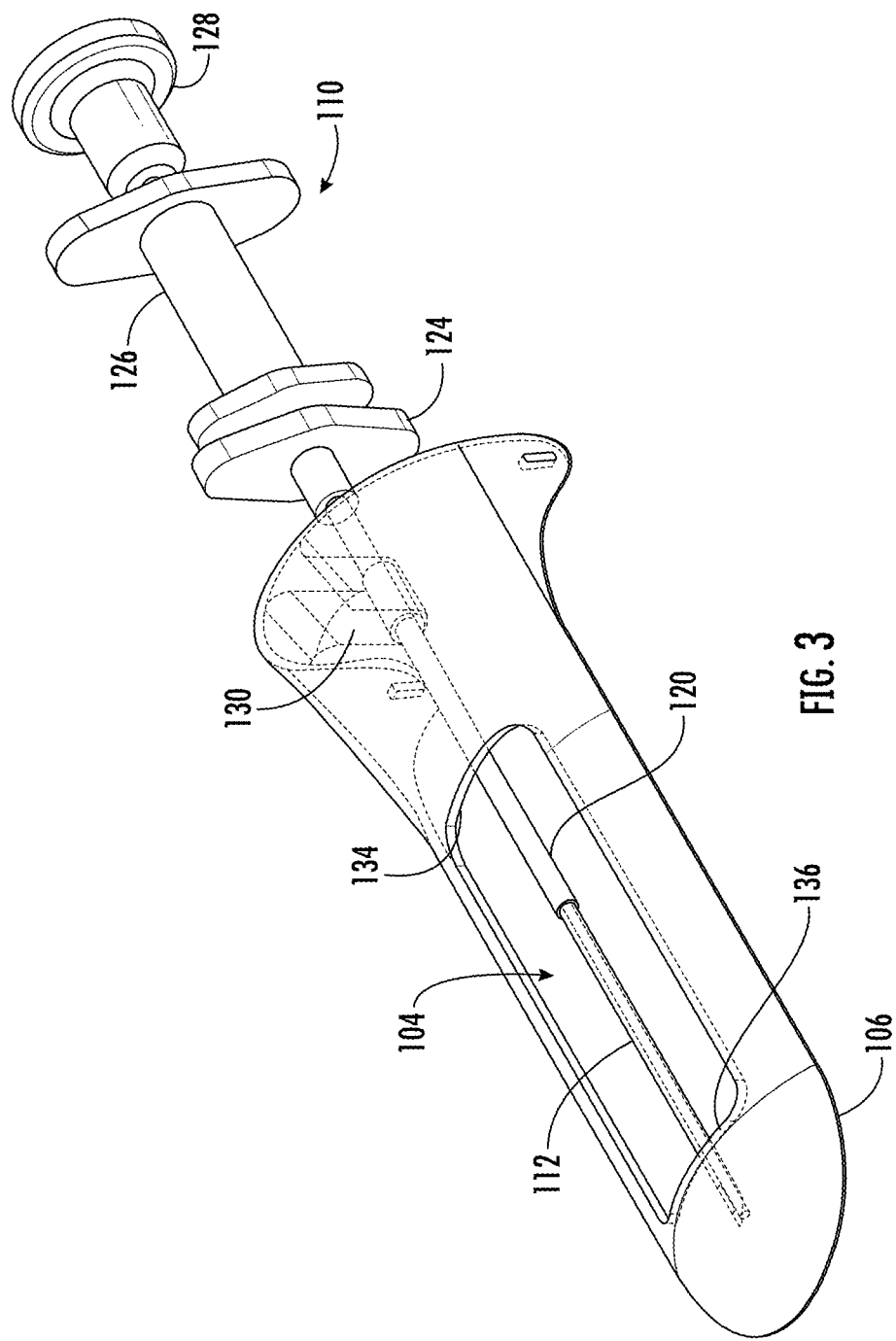
FIG. 3 is a perspective view of the speculum used together with the suturing instrument and the needle cannula passing through the speculum.
Figure 5A:
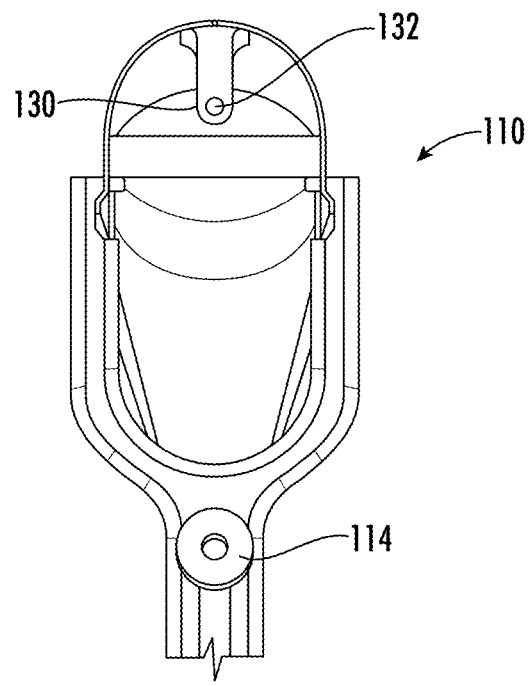
FIG. 5A is a rear view of the speculum, constructed in accordance with an embodiment of the invention.
Figure 5B:
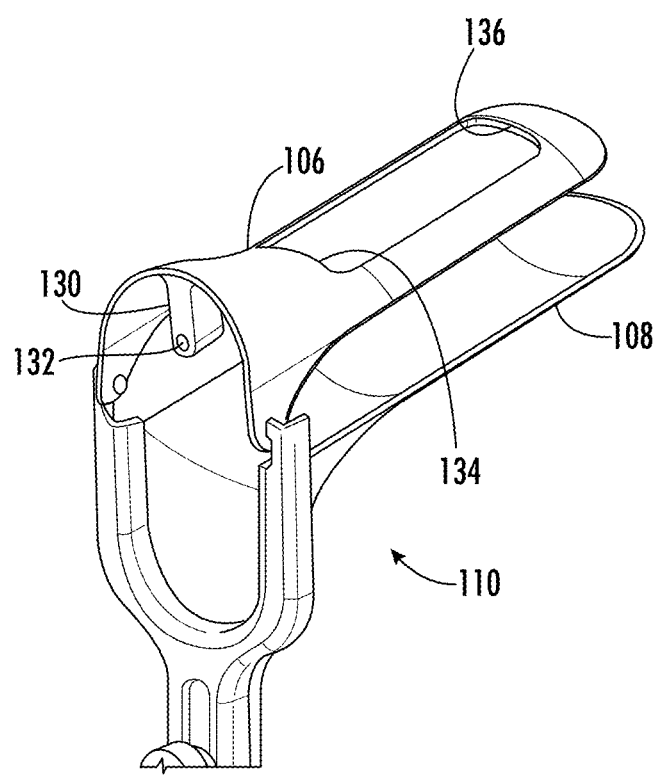
FIG. 5B is a perspective view of the speculum, constructed in accordance with an embodiment of the invention.

FIG. 1 is a perspective view of a transvaginal lift device 100 showing a speculum 102 with an opening/window 104 assembled to a suturing instrument 110, in accordance with an embodiment of the invention. FIG. 2 is a side view of the transvaginal lift device 100 as it is used with the suturing instrument 110 and the needle cannula 112 passing through the speculum 102 and showing an enlarged view of the speculum 102, while FIG. 3 is a perspective view of the speculum 102 used together with the suturing instrument 110 and the needle cannula 112 passing through the speculum 102, according to an embodiment of the invention. FIGS. 5A and 5B show a rear view and perspective view, respectively of the speculum 102, constructed in accordance with an embodiment of the invention.

Figure 11:
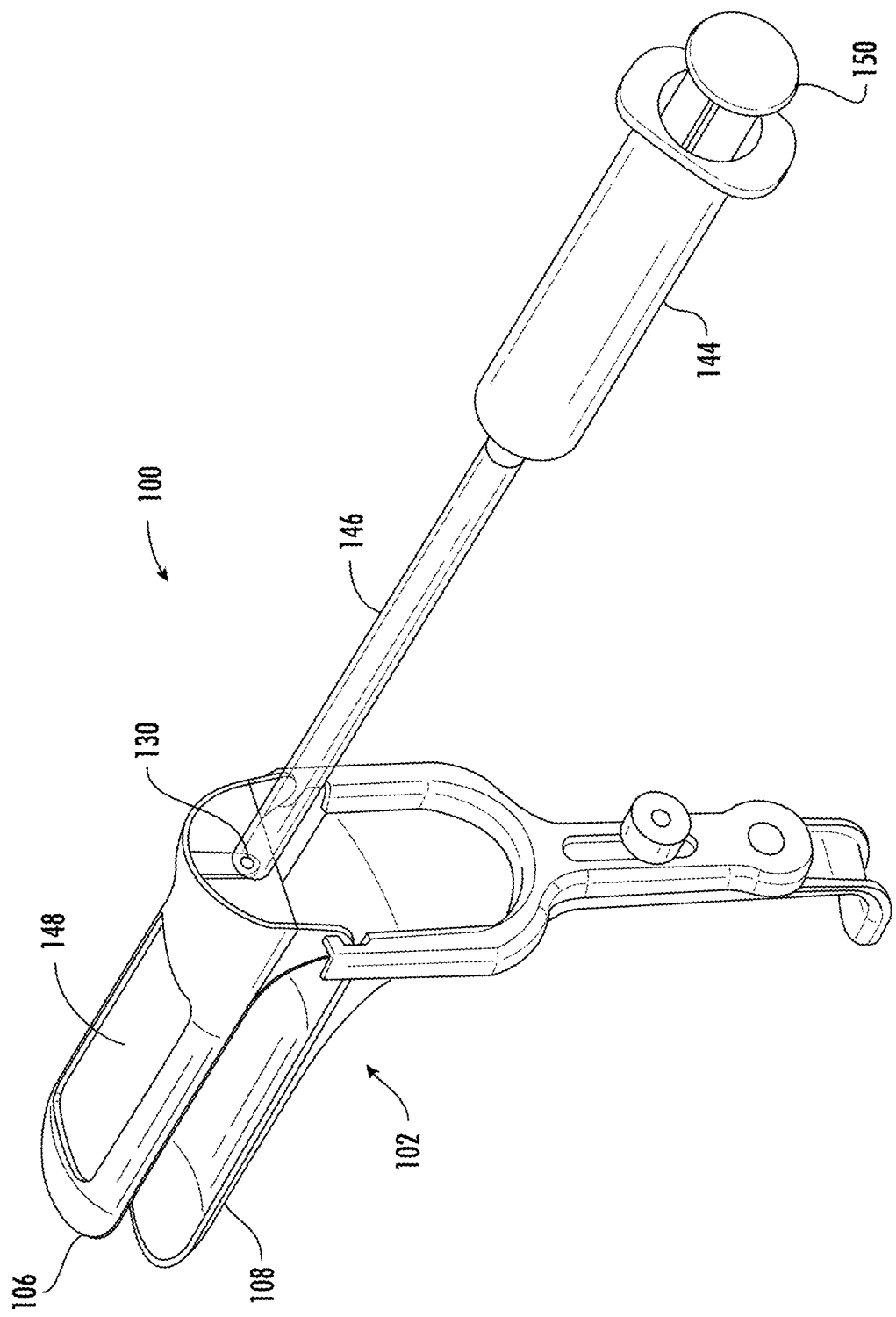
FIG. 11 shows a rear view of the speculum that includes a vacuum system using a syringe, in accordance with an embodiment of the invention.
Figure 12:
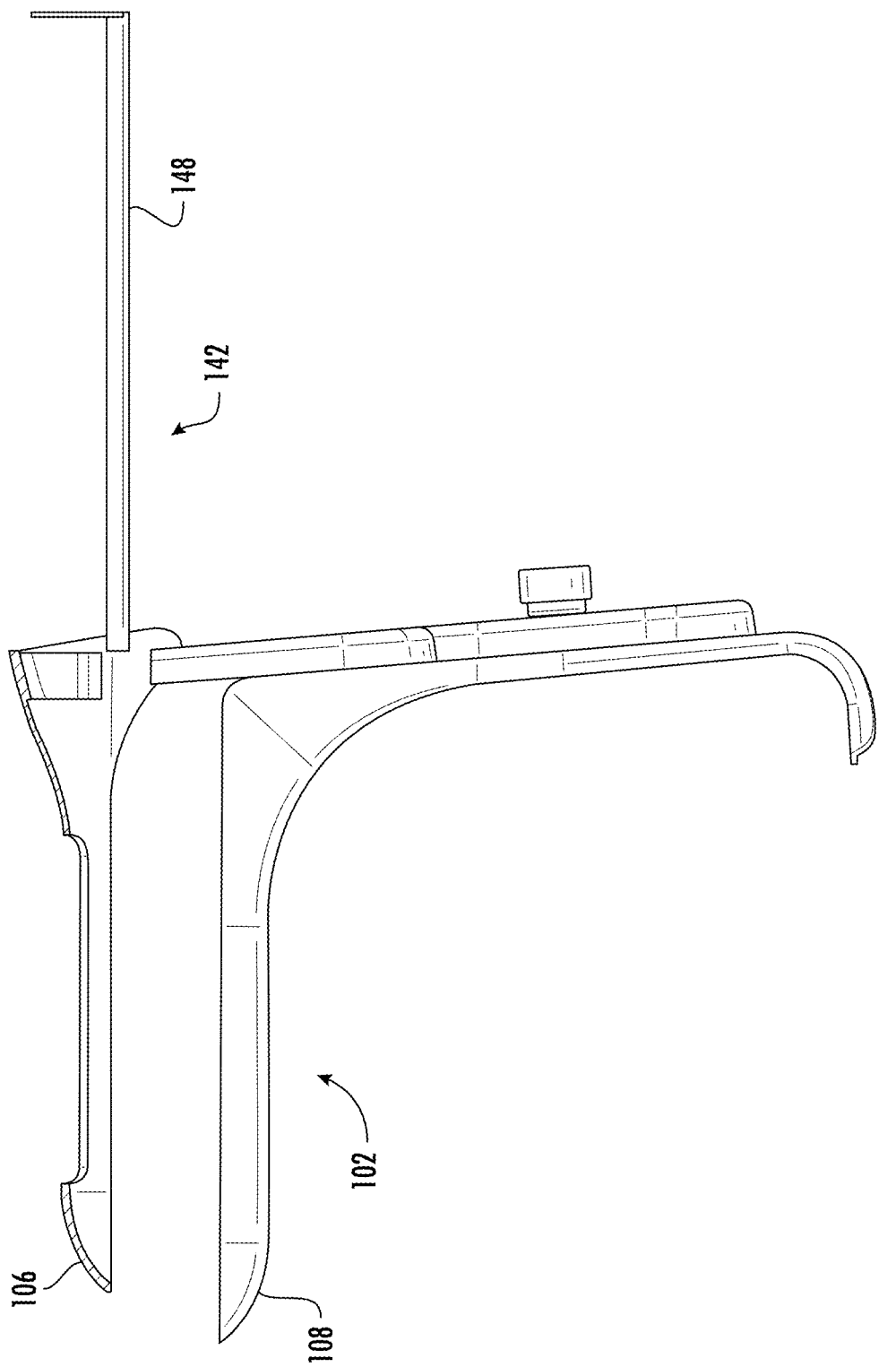
FIG. 12 shows a side view of the removed embodiment piece from the speculum, used to generate the vacuum inside the upper vane, in accordance with an embodiment of the invention.

FIGS. 11 and 12 are rear and side views, respectively, of the speculum 102, which includes the vacuum system 142 in the upper vane 106 of the speculum 102. In particular embodiments, the vacuum system 142 generates a vacuum using a syringe 144. In alternate embodiments, the vacuum is generated using compressed air. Also shown, in the embodiment of FIG. 12, is a speculum cover 148 prior to its attached to the upper vane 106. In operation, the syringe 144 is coupled to a tube 146 that connects to an opening into an interior space of the upper vane 106 (as defined by the upper vane 106 and attached speculum cover 148) in order to generate a suction or pulling force at the opening/window 104 into the interior space.

The speculum 102 has an upper vane 106, with a vacuum system 142, which includes the aforementioned opening or opening/window 104, a lower vane 108, and a handle 116. The upper and lower vanes 106, 108 are connected at a rear end of the two vanes 106, 108. The two vanes 106, 108 are moveable with respect to the aforementioned connected rear ends. The vanes 106, 108 are used for opening and closing a vagina so that a diagnosis channel is formed between the two vanes 106, 108 and the prolapsed tissue is pulled into the opening/window 104 with the vacuum system 142 located in the upper vane 106. In the embodiment shown, the upper and lower vanes 106, 108 are attached at the rear end such that the two vanes 106, 108 move between a closed position and an open position. In alternate embodiments, the vacuum system 142 is located between the upper and lower vanes 106, 108 or in the opening/window 104.

Figure 13:
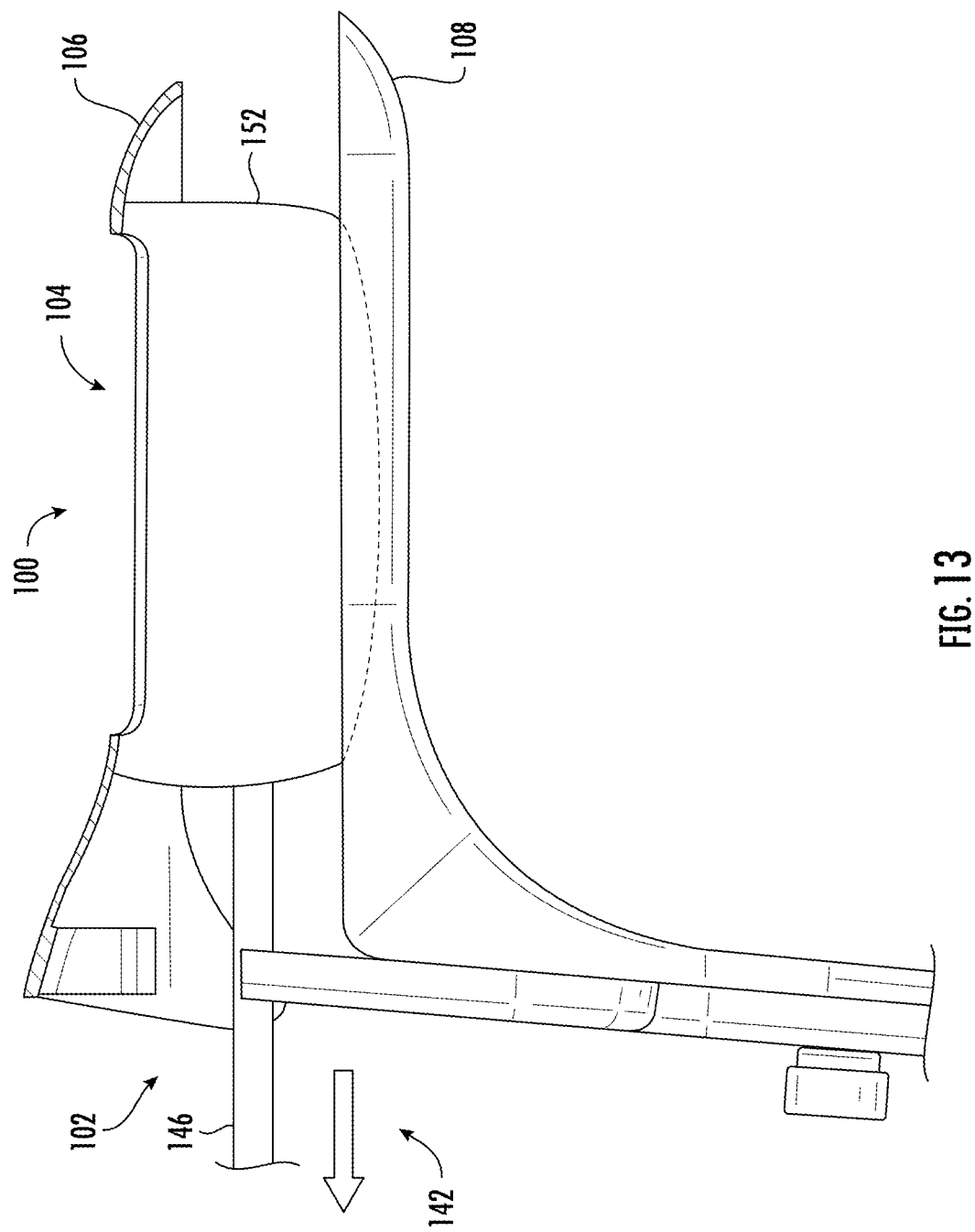
FIG. 13 is a plan view showing an exemplary arrangement for the speculum in which the vacuum system is disposed between the upper and lower vanes, according to an embodiment of the invention.

In an alternate embodiment, such as that shown in FIG. 13, which is a plan view of the transvaginal lift device 100 with the vacuum system 142 disposed between the upper and lower vanes 106, 108. In the embodiment shown, the vacuum system 142 includes a vacuum chamber 152 that extends from the upper vane 106 to the lower vane 108. The vacuum chamber 152 has an opening that coincides with the opening/window 104. Further, the vacuum chamber 152 has an airtight seal to the upper vane 106, most likely at, or near, the perimeter of the opening/window 104. As shown in FIG. 13, the tube 146 for suctioning air from the vacuum chamber 152 may be connected to a proximal end of the vacuum chamber 152. The end of the tube 146, opposite the end connected to the vacuum chamber 152, may be connected to a syringe 150 (see FIG. 11) or a compressed air vacuum arrangement.

Figure 14:
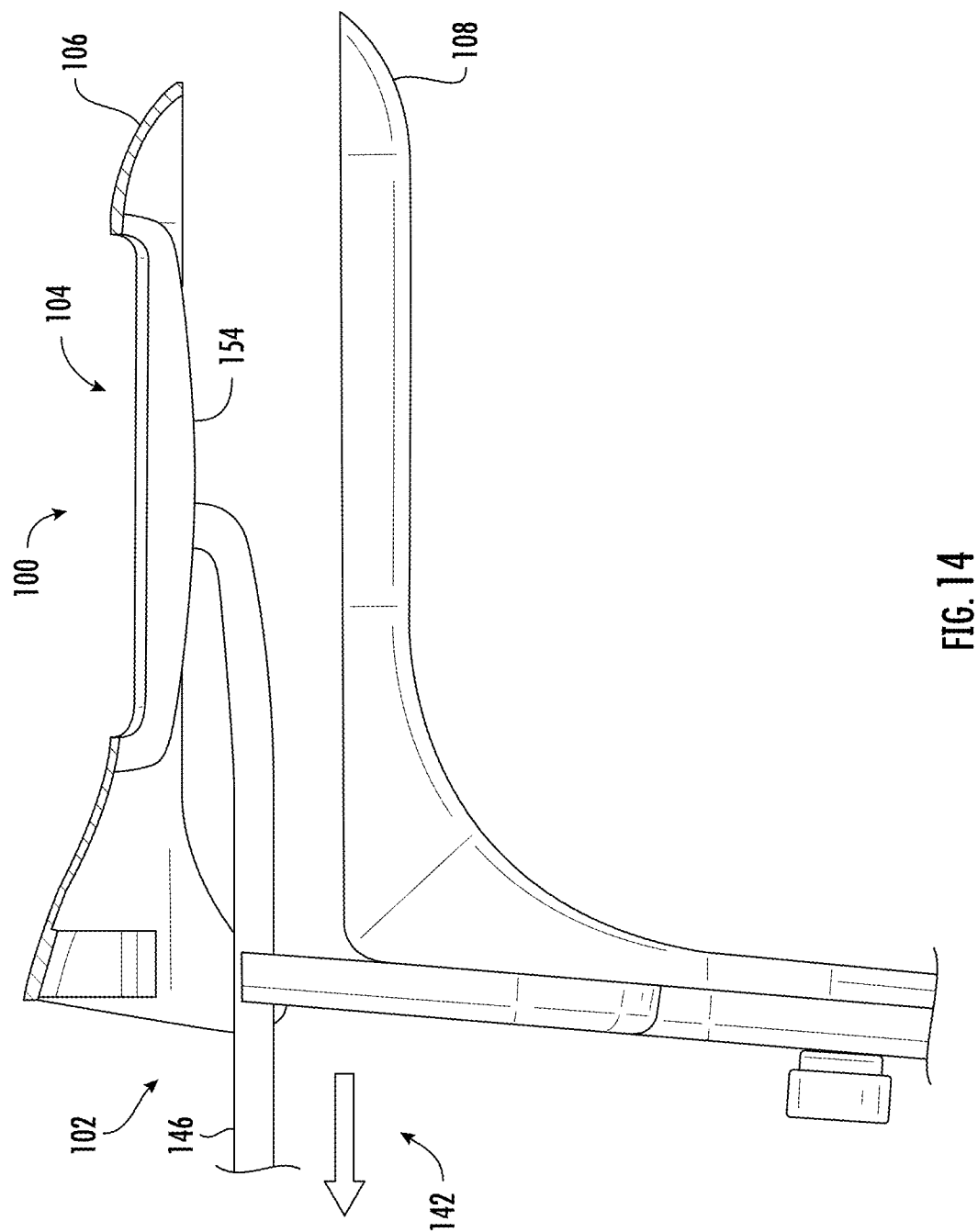
FIG. 14 is a plan view showing an exemplary arrangement for the speculum in which the vacuum system is disposed in the opening/window in the upper vane, according to an embodiment of the invention.

FIG. 14 is a plan view of the transvaginal lift device 100 showing another alternate embodiment, in which the vacuum system 142 is disposed at the opening/window 104. In this embodiment, a smaller vacuum chamber 154 (compared to that of FIG. 13) is largely confined to the upper vane 106. As shown in FIG. 14, the tube 146 for suctioning air from the vacuum chamber 154 may be connected to a middle section of the vacuum chamber 154. The end of the tube 146, opposite the end connected to the vacuum chamber 154, may be connected to a syringe 150 (see FIG. 11) or a compressed air vacuum arrangement.

Figure 15:
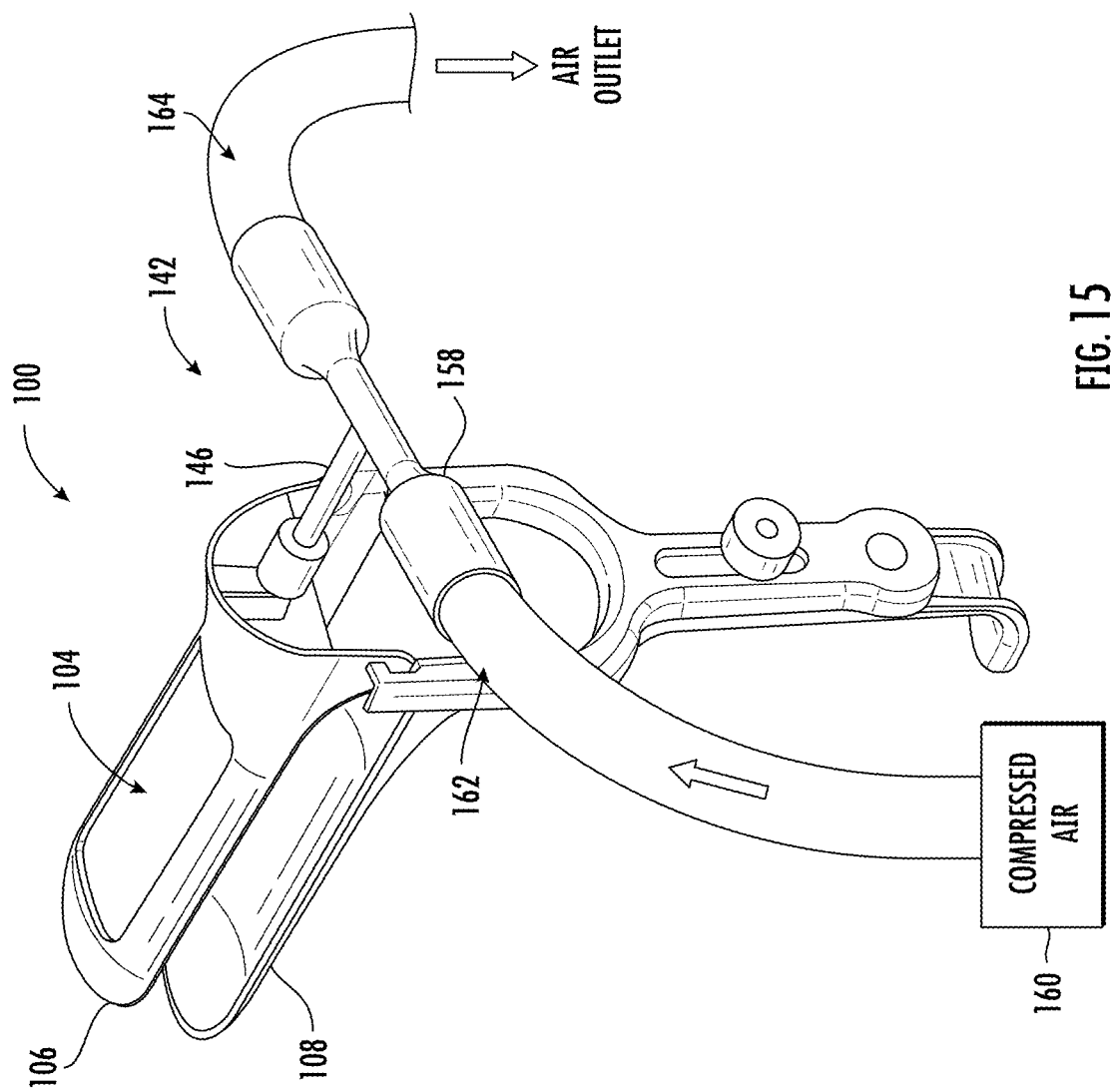
FIG. 15 is a plan view showing an exemplary arrangement of the speculum in which the vacuum system uses compressed air to generate the vacuum, in accordance with an embodiment of the invention.

FIG. 15 is a plan view of the transvaginal lift device 100 with a vacuum system 142 created using a compressed air system. The vacuum system 142 includes a venturi tube 158 (i.e., a tube with a short, relatively narrow center section and relatively wider end sections). One end of the venturi tube 158 is connected to a source of compressed air 160. The vacuum system 142 may also include any of the vacuum chambers 152, 154 illustrated in FIGS. 13 and 14, or the vacuum chambers as illustrated in FIGS. 11 and 12. In the vacuum system of FIG. 15, the venturi tube 158 is coupled to the vacuum chamber in the upper vane 106 via tube 146, which is also coupled to the relatively narrow center section of the venturi tube 158. The compressed air source 160 provides a flow of air to an inlet 162 of the venturi tube 158. As the air flows through the venturi tube 158 through the narrow center section towards the outlet 164, a vacuum is created such that suction is created in the vacuum chamber of upper vane 106 via the tube 146.

In the embodiment shown, the upper and lower vanes 106, 108 are elongate, and somewhat curved. The illustrated upper and lower vanes 106, 108 are convex, or outwardly curved such that even when the two vanes 106, 108 are in the closed position, i.e., the two vanes 106, 108 touching or at the closest distance along the entire length of the vanes 106, 108, there is an interior space created between the vanes 106, 108. It is within this interior space that the suturing instrument 110 operates. While the two vanes 106, 108 may be of roughly equal length, in the embodiments shown, the lower vane 108 is slightly longer than the upper vane 106 with the vacuum system 142 though, in alternate embodiments, the reverse may be true.

Additionally, the upper vane 106 with the vacuum system 142 has the opening/window 104, which is designed to pull and access prolapsed tissue. In the embodiments shown, the opening/window 104 is rectangular, however, it is envisioned that, in other embodiments, the opening/window 104 is circular or elliptical. In a particular embodiment, the lower vane 108 has an adjusting screw 114 that sets the extent of the opening position of the speculum 102. In a particular embodiment, tightening the adjusting screw 114, sets a position of the upper and lower vanes 106, 108 such that the position of the upper vane 106 with the vacuum system 142 with respect to the lower vane 108 does not change, and the distance between the front ends of the two vanes 106, 108 is fixed and constant.

In other embodiments, the upper vane 106 with the vacuum system 142 and/or the lower vane 108 includes a lighting element to improve visibility for the surgeon. The lighting element may be an LED or similar energy-efficient light source. In some particular embodiments of the invention, the lower vane 108 is provided with the lighting element to provide lighting for the surgeon to facilitate the medical procedure. In particular embodiments, the lighting element is powered by a battery in the speculum handle 116 or in one of the two vanes 106, 108.

Figure 4:
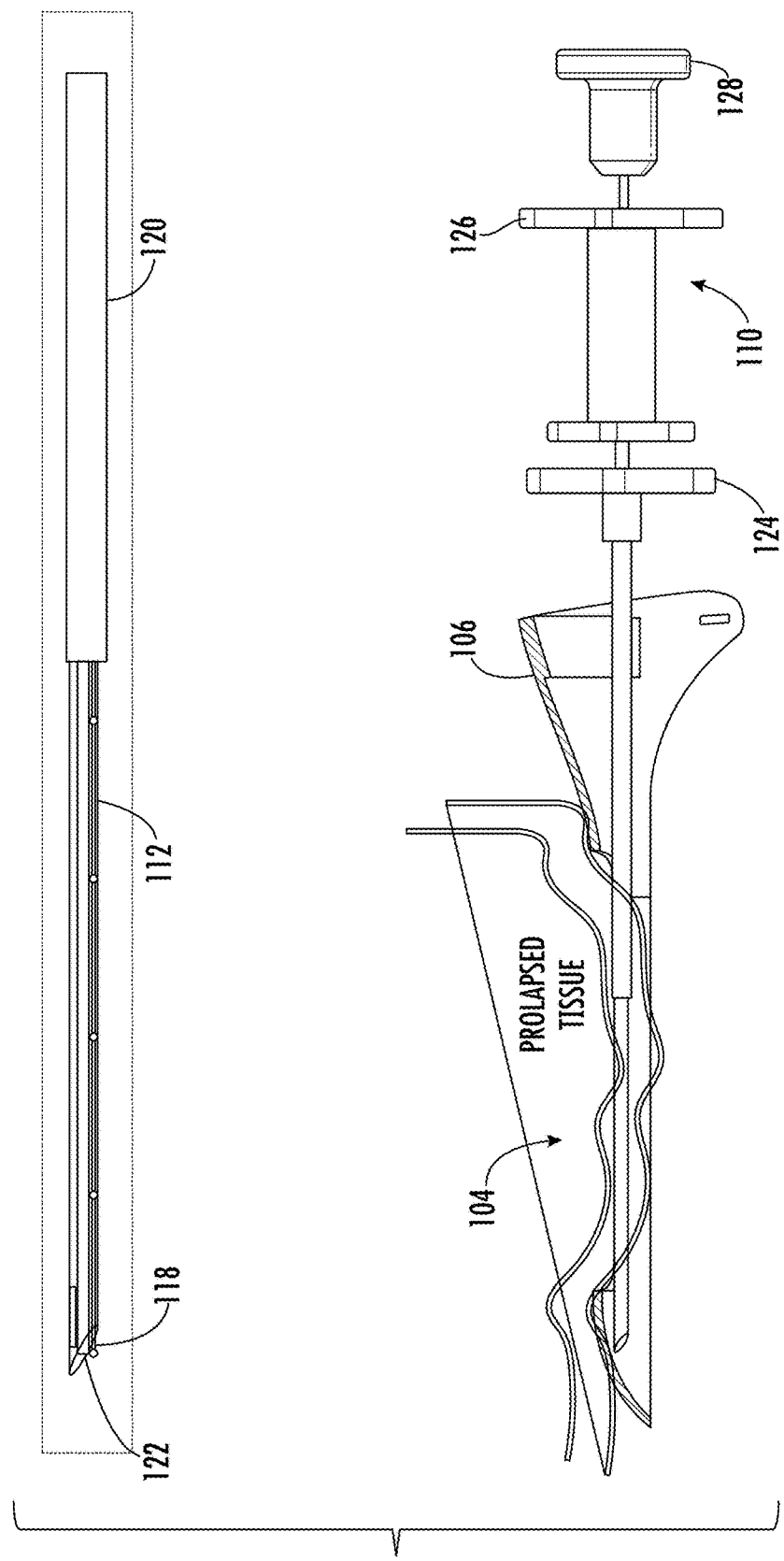
FIG. 4 is a plan view showing portions of the transvaginal lift device, according to an embodiment of the invention.
Figure 6:
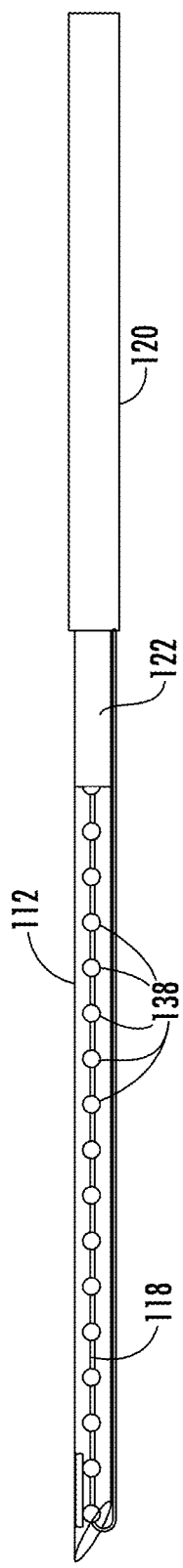
FIG. 6 is an exemplary embodiment of the suturing instrument with the suture assembled inside the needle cannula, according to an embodiment of the invention.

FIG. 4 is a plan view showing portions of the transvaginal lift device 100 with speculum 102 and suturing instrument 110, according to an embodiment of the invention. FIG. 6 is an exemplary embodiment of the suturing instrument 110 with the suture 118 assembled inside the needle cannula 112, according to an embodiment of the invention. As can be seen in FIGS. 4 and 6, the medical suturing instrument 110 has the needle cannula 112 and needle cannula handle 126, an external pusher cannula 120 and external pusher cannula handle 124, an inner pusher rod 122 and inner pusher rod handle 128, and the suture 118.

The medical suturing instrument 110 works by tightening the vaginal wall with a suture or implant 118 to reduce the vaginal prolapse. The transvaginal lift device 100 deploys and tightens the suture or implant 118. The suture 118 may be deployed during the insertion of the needle cannula 112 or when the needle cannula 112 is taken out, depending on the system configuration. The suture or implant 118 implanted in the body is biocompatible (bioresorbable, non-resorbable, elastomeric, or non-elastomeric). The suture 118 is preassembled inside the needle cannula 112 pass freely inside or outside the cannula 112. The sutures 118 may have knots, beads, or different shaped anchors 138 along its length to improve the tension on the vaginal wall, and these knots, beads, or anchors 138 operate so as to tighten or tension prolapsed the tissue with the knots, beads, or anchors 138 positioned at the proximal and distal ends to maintain the tension.

The anchors 138 may be shaped differently depending on the particular suturing technique or application being used. For example, the anchor 138 may be cylindrical or spherical like a bead 138. In this way, the bead 138 is just a specific type of anchor 138. Anchors 138 are not limited to these shapes, however cylindrical or spherical anchors 138 can easily move through the tubular needle cannula 112 when deployed using the inner pusher rod 122. The anchors or knots 138 (knots/beads) may be placed along the entire length of the suture 118, or only at the distal end and the proximal end of the suture 118.

In the configuration of FIG. 6, the lift device 100 works by inserting the needle cannula 112 through a guide 130 included in the speculum 102. In the embodiment shown, the guide 130 is formed on an inner surface at the rear end of the upper vane 106. The guide 130 (shown in FIGS. 5A and 5B) has an opening 132 (also shown in FIGS. 5A and 5B) through which the needle cannula 112 (along with the inner pusher rod 122 and suture 118 disposed within the needle cannula 112) is inserted to ensure that the suturing elements are properly positioned to pass through the exposed/prolapsed tissue. In the embodiment shown in FIGS. 11 and 12, the prolapsed tissue is suctioned into the opening/window 104 by the vacuum system 142 in a specific position. In the embodiments of FIGS. 11 and 12, the vacuum is generated with a syringe 144.

As can be seen, the syringe 144 is coupled to a tube 146 that connects to the guide 130. A speculum cover 148 is attached to the upper vane 106 and provides a vacuum seal where it is attached to the upper vane 106. In the embodiment shown, the vacuum seal is on the bottom and rear portions of the upper vane 106. However, in alternate embodiments, the tube 146 could be coupled to any opening into the interior space between the upper vane 106 and speculum cover 148. Thus, when the plunger 150 is removed from the syringe 144, a suction is created at the opening/window 104 to pull prolapsed tissue into the opening such that it can be sutured and/or anchored to effect repair of the prolapsed tissue. This reduces the risk of inadvertently perforating some other organ during the suturing procedure. The external pusher cannula 120 may also be inserted through the opening 132. In this way, the speculum 102 provides the necessary support, in the form of the guide 130, to maintain and fix, or place, the suture 118 in a specific position to standardize the placement of the suture 118. The embodiment of FIG. 6 shows a suture 118 with knots or spherical anchors/beads 138 for performing the tightening or tensioning of the prolapsed tissue.

During use of the lift device 100, the needle cannula 112 is inserted through the prolapsed tissue protruding by vacuum or gravity through the opening/window 104 of the speculum 102. The needle cannula 112 first pierces the prolapsed tissue at proximal end 134 of the opening/window 104 until it emerges from the tissue at the distal end 136 of the opening/window 104. As illustrated in FIG. 6, there may be a portion of the suture 118, with no knots or beads 138, positioned outside of the needle cannula 112. The outside portion of the suture 118 rests on the outer surface of the needle cannula 112 during insertion of the needle cannula 112 through the prolapsed tissue. This outside portion of the suture 118 typically remains in the tissue after the needle cannula 112 is removed and the proximal knot or anchor 136 is deployed.

The needle cannula 112 is manually manipulated using the needle cannula handle 126 and inserted into the tissue. The inner pusher rod 122 is used to deploy one or more anchors or knots 138 first at a distal end of the needle cannula 112 to tension that end of the prolapsed tissue. The inner pusher rod 122 is manually manipulated using the inner pusher rod handle 128. Then, the needle cannula 112 is inserted further until the needle cannula 112 is completely inserted and reaches the distal end 136 of the opening/window 104 of the speculum 102. Following insertion of the needle cannula 112, the suture 118 and any knots or anchors 138 at the distal end are deployed using the inner pusher rod 122. Following this deployment, the user may rotate the needle cannula handle 126 to increase the size of the knot 138 in the suture 118. After the distal anchor 138 is deployed, the needle cannula is removed from the prolapsed tissue.

Figure 8:
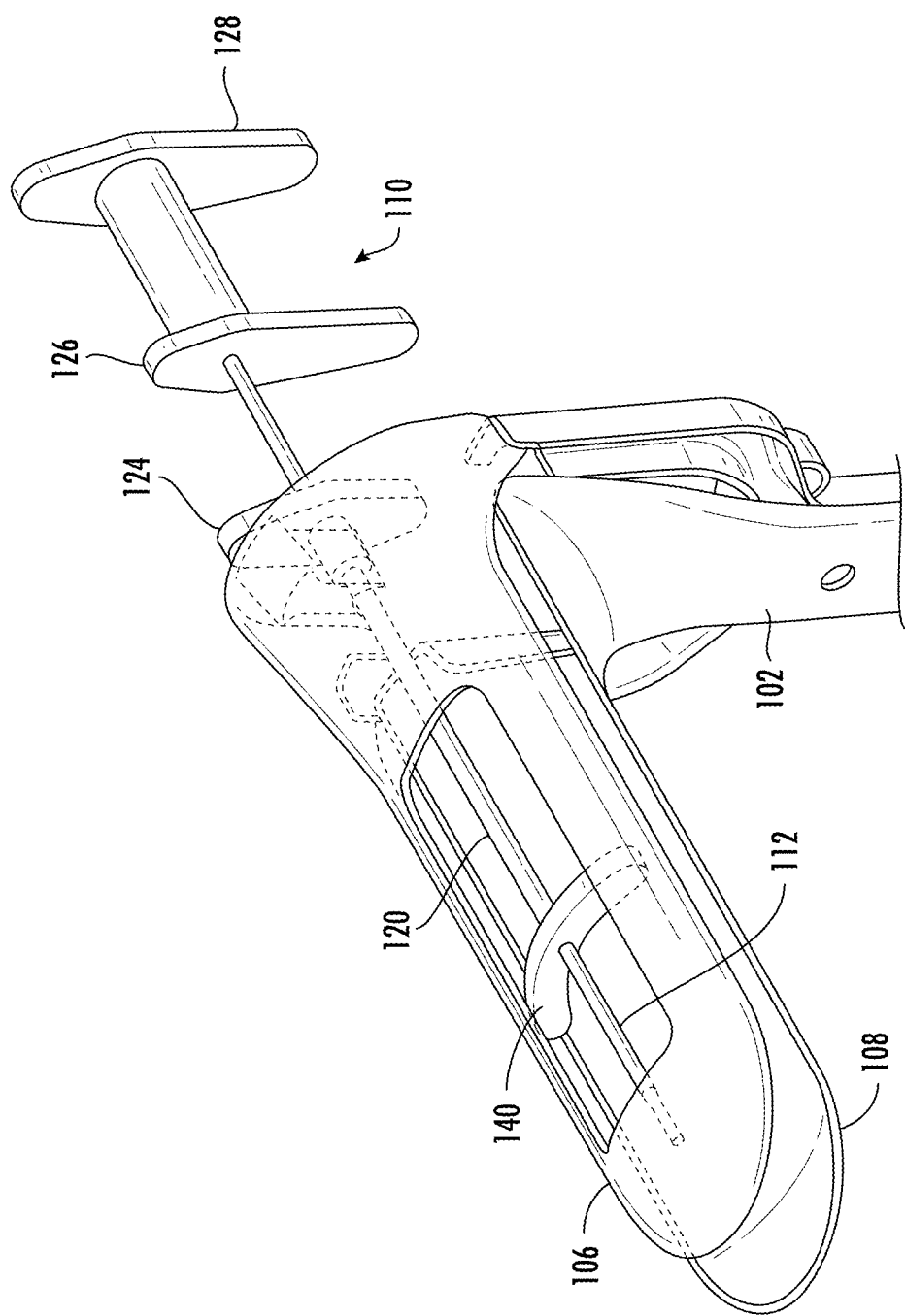
FIG. 8 is perspective view of a transvaginal lift device with a pusher bar, in accordance with an embodiment of the invention.

The external pusher cannula 120 is used to support the tissue when the needle cannula 112 and inner pusher rod 122 are removed. Further, the external pusher cannula 120 is used inside the body to tighten suture 118 in the prolapsed tissue, which may be suctioned as described above. This may be accomplished with the aid of a pusher bar 140 on the distal end of the external pusher cannula 120 to secure and support the prolapsed (by suction or gravity) tissue during tensioning. FIG. 8 show an embodiment of the lift device 100 that includes the pusher bar 140. Once suturing is completed, the external pusher cannula 120 is removed and the anchors or knots 138 are designed to support the tension and create a lifting line that tightens and lifts the prolapsed tissue.

Figure 7:
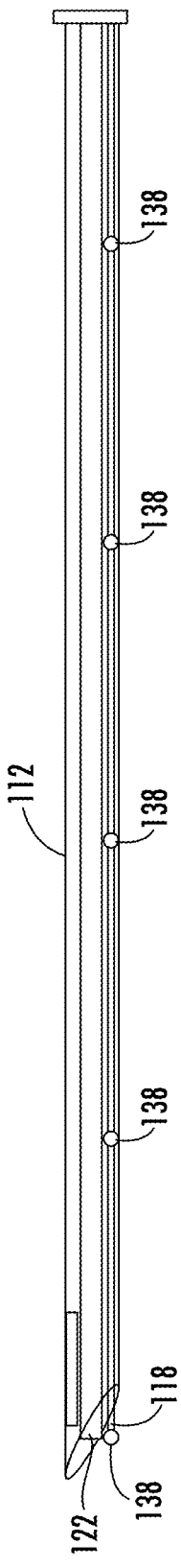
FIG. 7 is an alternate embodiment of the suturing instrument with the suture assembled inside the needle cannula, according to an embodiment of the invention.

As referenced above, the suturing component of the lift device 100 works in different ways and in many different configurations. All methods and configurations depend on the speculum 102 to open the vagina. When the vagina is opened using the speculum 102, the opening/window 104 in the speculum 102 with a vacuum system 142 suctions and exposes the excess or prolapsed tissue. FIG. 7 is an alternate embodiment of the suturing instrument 110 with the suture 118 assembled inside the needle cannula 112, according to an embodiment of the invention.

In the configuration of FIG. 7, the lift device 100 works by inserting the needle cannula 112 through the guide 130 included in the speculum 102. As explained above, the guide 130 ensures the needle cannula 112 passes through the exposed prolapsed tissue. The needle cannula 112 is inserted through the tissue close to the proximal end 134 of the window 104 of the speculum 102. The inner pusher rod 122 and the suture 118 with the designated number of anchors or knots 138 are preassembled inside the needle cannula 112. When the needle cannula 112 is completely inserted and reaches the distal end 136 of the opening/window 104, the inner pusher rod 122 deploys the suture 118 with the distal anchor or knot 138 at the distal end 136. Then, the needle cannula 122 and the inner pusher rod 122 are removed leaving the suture 118 inside the tissue and allowing for deployment of the proximal anchor or knot 138 at the proximal end 134 of the opening/window 104.

The external pusher cannula 120 is used to support the tissue when the needle cannula 112 and the inner pusher rod 122 are removed. Moreover, the external pusher cannula 120 is maintained inside the vagina in order to lift and tighten the tissue. Finally, the external pusher cannula 120 is removed and the anchors or knots 138 are designed to support the tension and creates a lifting line that tightens and lifts the prolapsed tissue.

In either of the configurations described above, the delivery system for the suture 118 is a needle cannula 112 (for example, in different sizes ranging from 80 millimeters up to 200 millimeters), which has an inner pusher rod 122 used to deploy the suture 118, and an external pusher cannula 120 to push and tighten the tissue. The external pusher cannula 120 is manually manipulated using the external pusher cannula handle 124. The lift device 100 contains an amount of suture 118 (e.g., bioresorbable or non-resorbable) which is placed inside the vaginal wall using the needle cannula 112 and then it is pulled to tighten and lift the prolapsed vaginal wall.

During the procedure, the needle cannula 112 that holds the suture 118 is inserted along the targeted area. At one end, the suture 118 is anchored carefully to the firmer underlying structures, whereas the other end of the suture 118 goes inside the vaginal wall following a predetermined path until the suture 118 reaches the desired endpoint. When the needle cannula 112 is withdrawn, the suture 118 and the anchors 138 contained therein are deposited effectively into the vaginal wall. During the procedure, the surgeon may pull and rotate the needle cannula 112 to improve the elevation of the prolapsed tissue so that the tissue can be set into a tightened, more lifted position.

Typically, the bioresorbable or non-resorbable, elastomeric or non-elastomeric suture or implant 118, is different according to the type and brand. The suture or implant 118, placed inside vaginal wall, causes a mild inflammatory reaction, which leads to collagenization and increased circulation. Thus, a scaffold in the vaginal wall area is formed that keeps the vaginal wall tightened. If the suture 118 is resorbable, after the absorption process, the collagen produced is responsible for the improvement or lifting of the vaginal wall.

Figure 9:
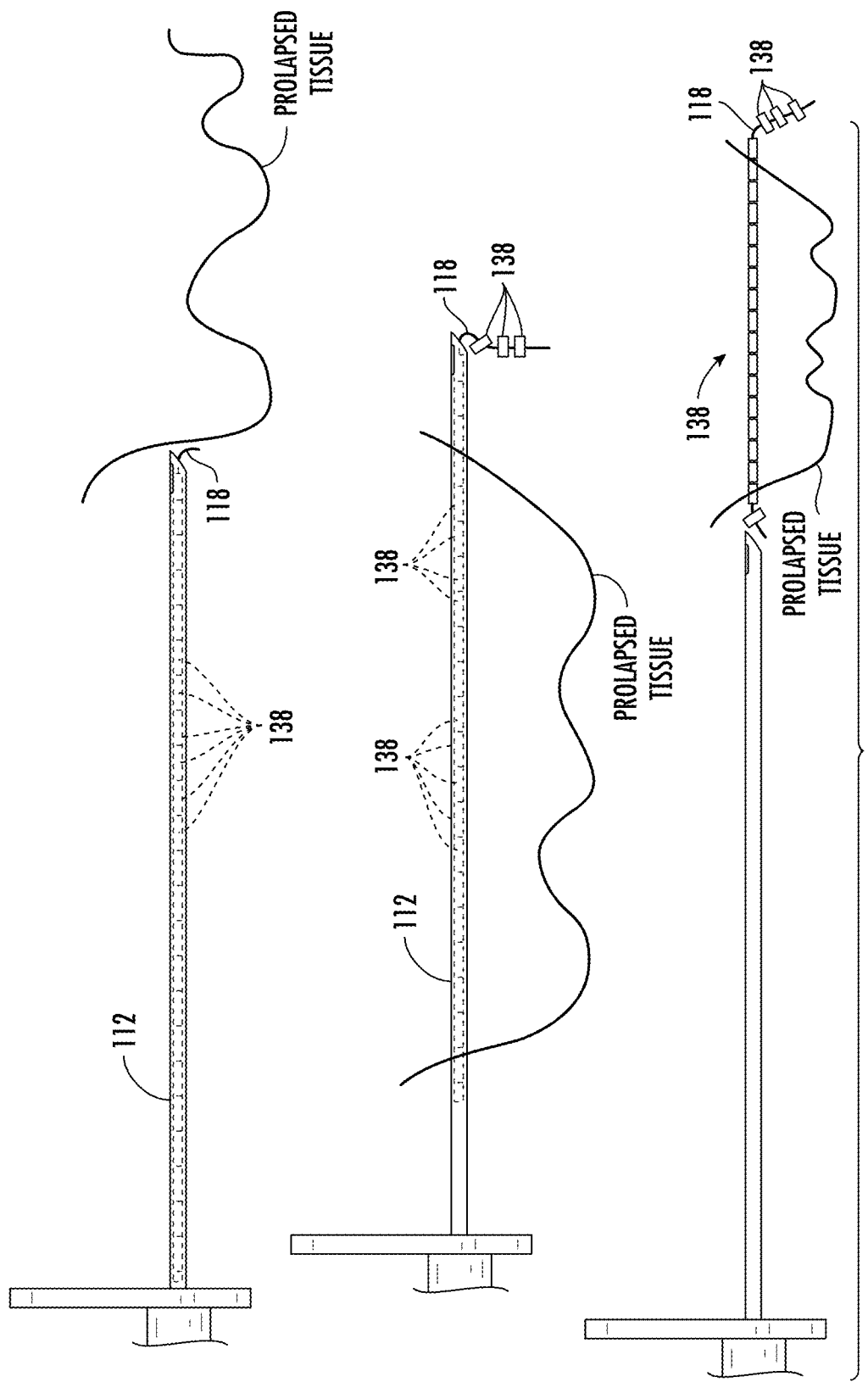
FIG. 9 shows an exemplary suturing or implant arrangement, according to an embodiment of the invention.
Figure 10:
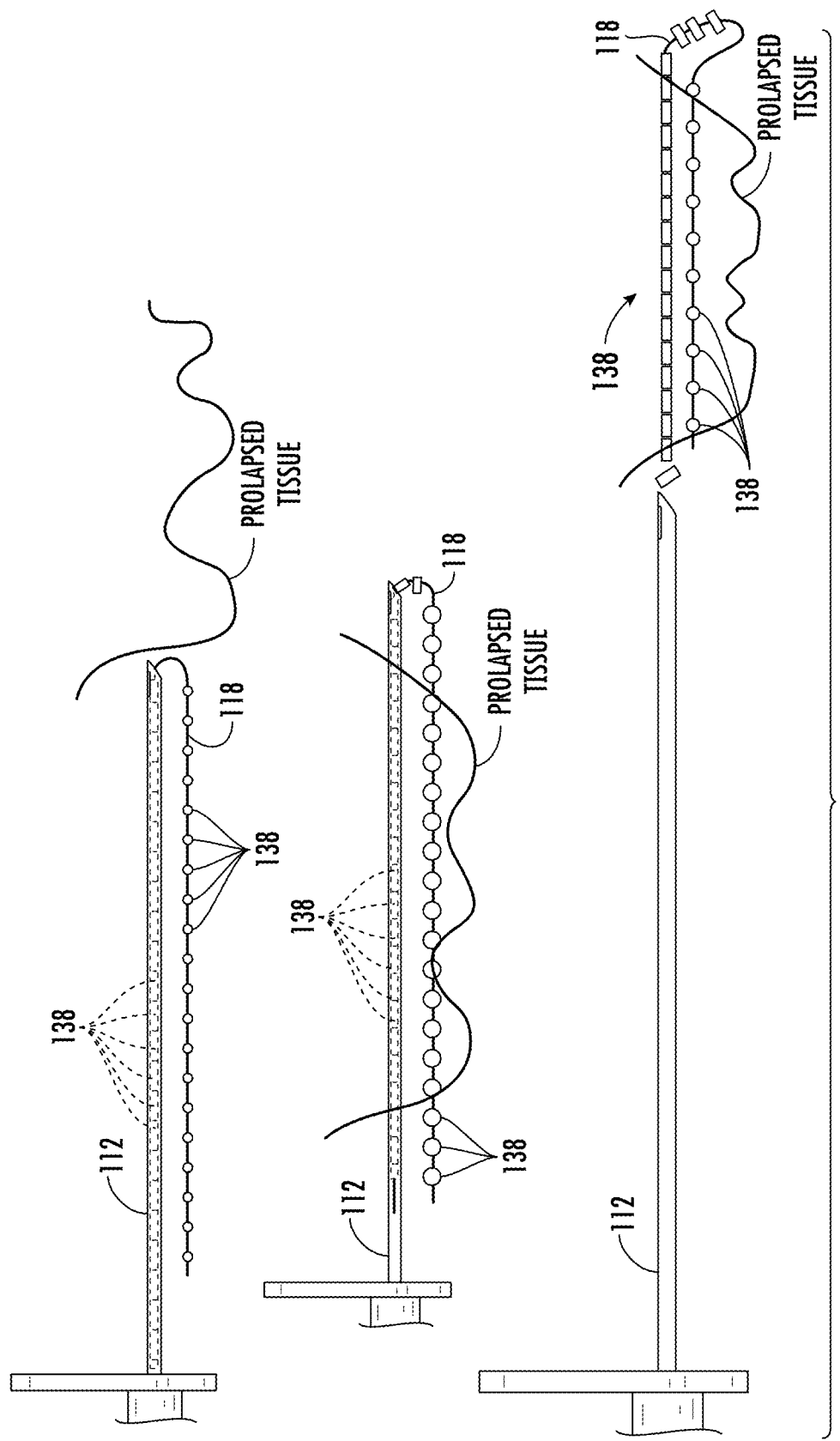
FIG. 10 shows another exemplary suturing or implant arrangement, according to an embodiment of the invention.

FIGS. 9 and 10 show exemplary suturing arrangements somewhat different from those described above. In the arrangement of FIG. 9, the suture 118 has a series of attached cylindrical anchors 138 staged within the needle cannula 112. In the embodiment shown, the cylindrical anchors 138 are placed end-to-end such that they fill the entire needle cannula 112. However, it is also envisioned that some arrangements will have the cylindrical anchors 138 spaced farther apart than shown in FIG. 9.

The top image of FIG. 9 shows the needle cannula 112 prior to insertion through the suctioned/prolapsed tissue. The middle image of FIG. 9 shows the needle cannula 112 after insertion through the prolapsed tissue. The inner pusher rod 122 used to deploy the one or more cylindrical anchors 138 at the distal end. Following deployment, the cylindrical anchors 138, which are attached to the suture 118 at a central part of the cylinder, rotate slightly so that the circular wall of the cylinder abuts the prolapsed tissue. The bottom image of FIG. 9 shows the needle cannula 112 after removal from the prolapsed tissue. Anchors 138 are deployed at the proximal end and, in concert with the anchors 138 at the distal end, are used to tension the prolapsed tissue. As shown in FIG. 9, a number of anchors 138 remain inside the prolapsed tissue after suturing.

In the arrangement of FIG. 10, the suture 118 has the series of attached cylindrical anchors 138 staged within the needle cannula 112, similar to that of FIG. 9. In the embodiment shown, the cylindrical anchors 138 are also placed end-to-end such that they fill the entire needle cannula 112. However, as explained above, it is envisioned that some arrangements will have the cylindrical anchors 138 spaced farther apart than shown in FIG. 10. But unlike FIG. 9, the suture arrangement of FIG. 10 includes a portion of the suture 118 located outside of the needle cannula 112, that portion having one or more attached knots or beads 138.

The top image of FIG. 10 shows the needle cannula 112 prior to insertion through the prolapsed tissue. The middle image of FIG. 10 shows the needle cannula 112 after insertion through the prolapsed tissue. The inner pusher rod 122 used to deploy the one or more of the cylindrical anchors 138 at the distal end. As shown, there will also be one or more knots or beads 138 at an outer surface of the distal end of the prolapsed tissue. The bottom image of FIG. 10 shows the needle cannula 112 after removal from the prolapsed tissue. Anchors 138 are deployed at the proximal end of the prolapsed tissue and, in concert with the anchors 138 at the distal end, are used to tension the prolapsed tissue. The knots or beads 138 at the distal end also help tension the prolapsed tissue at the distal end. As shown in FIG. 10, a number of anchors and knots/beads 138 remain inside the prolapsed tissue after suturing.

Another possible suturing arrangement not shown in the drawing, but which can be envisioned by those of ordinary skill in the art, involves the use of one or more wires attached to the suture 118 to function as anchors. Similar to the cylindrical anchors shown in FIGS. 9 and 10, the attached wires 138 can be staged end-to-end in the needle cannula 112. Following insertion of the needle cannula 112, one or more of the wires 138 are deployed at the distal end. After exiting the needle cannula 112, like the cylindrical anchors 138, the one or more wires 138, which are attached to the suture 118 at the central part of the wire 138, rotates slightly so that the entire length of the wire 138 abuts the prolapsed tissue.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A transvaginal lift device comprising:
    a speculum having an upper vane and a lower vane, the upper and lower vanes each being elongate with a front end and a rear end, the upper and lower vanes being attached at the rear end such that the vanes move between a closed position and an open position, and wherein the upper vane has an opening/window configured to allow prolapsed tissue to protrude through the opening/window into an interior portion of the speculum; and
    a suturing instrument with a needle cannula and a suture, wherein the suturing instrument is attached to the speculum, the suturing instrument configured to place the suture in the prolapsed tissue protruding through the opening/window;
    wherein the speculum includes a guide to fix a position of the needle cannula, and the guide is attached to the upper vane, wherein the guide has an opening through which the needle cannula is inserted.

2. The transvaginal lift device of claim 1, wherein the suturing instrument includes an external pusher cannula inside of which the needle cannula is disposed, the external pusher cannula configured to support the prolapsed tissue during a tensioning step.

3. The transvaginal lift device of claim 2, wherein the external pusher cannula has a handle for manual manipulation of the external pusher cannula.

4. The transvaginal lift device of claim 1, wherein the suturing instrument includes an inner pusher rod configured to be inserted within the needle cannula, the inner pusher rod configured to deploy the suture during suturing of the prolapsed tissue.

5. The transvaginal lift device of claim 4, wherein the inner pusher rod has a handle for manual manipulation of the inner pusher rod.

6. The transvaginal lift device of claim 4, wherein the needle cannula and the inner pusher rod are configured to deploy the suture having one or more attached anchors for tensioning of the prolapsed tissue.

7. The transvaginal lift device of claim 6, wherein the one or more attached anchors are cylindrical or spherical.

8. The transvaginal lift device of claim 6, wherein the one or more attached anchors are each made of one or more wires.

9. The transvaginal lift device of claim 4, wherein the needle cannula and the inner pusher rod are configured to deploy the suture having one or more knots in the suture along a length thereof, the one or more knots for tensioning of the prolapsed tissue.

10. The transvaginal lift device of claim 1, wherein the needle cannula has a handle for manual manipulation of the needle cannula.

11. The transvaginal lift device of claim 1, wherein the speculum includes a handle to control the opening and closing of the front ends of the upper and lower vanes.

12. The transvaginal lift device of claim 11, wherein the speculum handle includes an adjusting screw configured to fix the extent of the open position of the upper and lower vanes.

13. The transvaginal lift device of claim 1, further comprising a vacuum system assembled to the speculum, the vacuum system configured pull the prolapsed tissue through the opening/window.

14. The transvaginal lift device of claim 13, wherein the vacuum system is located in the upper vane, which has the opening/window.

15. The transvaginal lift device of claim 13, wherein the vacuum system includes a speculum cover attached to the upper vane, the speculum cover configured to provide a vacuum seal where it is attached to the upper vane.

16. The transvaginal lift device of claim 13, wherein the vacuum system is located between the upper and lower vanes.

17. The transvaginal lift device of claim 13, wherein the vacuum system is located in the opening/window.

18. The transvaginal lift device of claim 13, wherein the vacuum system is adjustable or removable with respect to the speculum.

19. The transvaginal lift device of claim 13, wherein the vacuum system generates a vacuum using a syringe.

20. The transvaginal lift device of claim 19, wherein the syringe is coupled via a tube to an opening into the upper vane.

21. The transvaginal lift device of claim 1, wherein the speculum includes a lighting element.

22. The transvaginal lift device of claim 21, wherein the lighting element is battery-powered.

23. The transvaginal lift device of claim 1, wherein the guide has an opening through which an external pusher cannula is inserted.

24. The transvaginal lift device of claim 1, wherein the guide has an opening through which an inner pusher rod is inserted.

25. The transvaginal lift device of claim 1, wherein the suture may be made of resorbable or non-resorbable, elastomeric or non-elastomeric material.

* * * * *